United States Patent [19]

Emmons et al.

[11] 4,143,020

[45] Mar. 6, 1979

[54] COPOLYMERS OF SULFONIC ACID MONOMERS

[75] Inventors: William D. Emmons, Huntingdon Valley; Graham Swift, Ambler, both of Pa.

[73] Assignee: Rohm and Haas Company, Philadelphia, Pa.

[21] Appl. No.: 882,521

[22] Filed: Feb. 23, 1978

Related U.S. Application Data

[62] Division of Ser. No. 273,886, Aug. 7, 1972, which is a division of Ser. No. 134,905, Apr. 16, 1971, Pat. No. 3,770,801.

[51] Int. Cl.² .......................... C08F 2/00; C08F 4/04; C08F 28/00
[52] U.S. Cl. .................... 260/29.6 SQ; 260/29.6 TA; 260/31.2 R; 260/33.6 UA; 260/875; 260/885; 526/81; 526/86; 526/287
[58] Field of Search ................ 260/29.6 TA, 29.6 SQ, 260/885, 875; 526/86, 287

[56] References Cited

U.S. PATENT DOCUMENTS

| | | | |
|---|---|---|---|
| 3,592,655 | 7/1971 | Dykstra | 526/287 |
| 3,711,449 | 1/1973 | Brendley | 526/287 |
| 3,751,451 | 8/1973 | Samour et al. | 260/29.6 TA |

FOREIGN PATENT DOCUMENTS 2155184  5/1973  Fed. Rep. of Germany .......... 526/287

*Primary Examiner*—Herbert J. Lilling

[57] ABSTRACT

The present invention is concerned with novel monomers containing sulfonic acid groups or salts thereof and polymers thereof which are useful for many purposes, such as antistatic agents for textiles and other shaped articles formed of hydrophilic materials. They are useful for making copolymers that are particularly valuable in coating compositions, especially in the form of aqueous latices or organic solvent solutions thereof. Examples of the monomers are of the formula

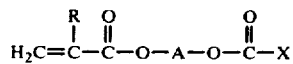

wherein R is hydrogen or lower ($C_1$-$C_4$)alkyl, such as methyl, A is an alkylene group having 2 to 10 carbon atoms, at least 2 of which extend in one chain between the oxygen atoms, and X is an aromatic nucleus or an alkyl group, substituted by a sulfonic acid group and optionally one or more groups selected from sulfonic acid, carboxylic acid, and lower alkyl, such as methyl, ethyl, propyl, or butyl.

12 Claims, No Drawings

COPOLYMERS OF SULFONIC ACID MONOMERS

This is a division of application Ser. No. 273,886 filed Aug. 7, 1972, which in turn is a division of Ser. No. 134,905, filed Apr. 16, 1971, now U.S. Pat. No. 3,770,801.

THE DISCLOSURE

The new monomers of the present invention are those of the general formula I as follows:

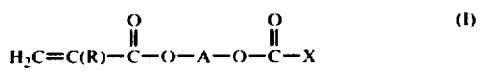

wherein R is hydrogen or lower ($C_1$-$C_4$)alkyl, preferably hydrogen or methyl, A is an alkylene group having 2 to 10 carbon atoms, at least 2 of which extend in a chain between the adjoined oxygen atoms, and X is either (1) an aromatic nucleus, such as a benzene or naphthalene ring, substituted by a sulfonic acid group and optionally one or more sulfonic acid or carboxylic acid groups, or (2) an alkyl group, substituted or unsubstituted, of the formula

wherein one of R' and $R^3$ is a sulfonic acid group and the other is H, $R^2$ is H or a ($C_1$-$C_4$)alkyl group, $R^4$ is H, —COOH, or a ($C_1$-$C_4$)alkyl group, and $R^5$ is H or a ($C_1$-$C_4$)alkyl group, with the proviso that only one of $R^2$, $R^4$ and $R^5$ is alkyl except that both $R^2$ and $R^4$ may be alkyl provided, in that case, R' and $R^5$ are both H.

Preferred monomers are those which contain both a carboxyl group and a sulfonic acid group. In these monomers the group X of formula II above is defined as follows X is either (1) an aromatic nucleus, such as a benzene or napthalene ring, preferably a benzene ring, substituted by a sulfonic acid group and a carboxylic group or (2) an alkyl group of the formula

wherein one of R' and $R^3$ is a sulfonic acid group and the other is H, $R^2$ is H or a ($C_1$-$C_4$)alkyl group, and $R^4$ is H or a ($C_1$-$C_4$)alkyl group.

Preferably, when one of $R^2$ and $R^4$ is an alkyl group, the other is H.

While the description so far recites that the monomers contain a sulfonic acid group and optionally a carboxylic acid group, it is to be understood that they may contain more than one sulfonic acid group and more than one carboxylic acid group and also that the salts of such monomers are also part of the present invention. The salts of the monomers may be formed with any basic material, organic or inorganic, such as an alkali metal or alkaline earth metal hydroxide, ammonium hydroxide, primary, secondary or tertiary amine, whether volatile or not, such as methylamine, dimethylamine, trimethylamine, the corresponding ethyl, propyl, isopropyl, n-butyl, isobutyl, and tertiary-butyl amines, monoethanolamine, diethanolamine, and triethanolamine, and quaternary ammonium bases, such as benzyltrimethylammonium hydroxide, and so on.

In general, the monomers of the present invention may be obtained in various ways but a preferred method is to react (1) a neutral alkyl ester of an α,β-monoethylenically unsaturated acid, such as acrylic acid, methacrylic acid, and itaconic acid in which the alkyl group or one of the alkyl groups contains 2 to 10 carbon atoms and a hydroxy group spaced by at least 2 carbon atoms from the ester linkage with (2) an anhydride of an organic carboxylic acid containing a sulfonic acid group.

The reactant (1) has the general formula IV as follows:

wherein the symbols are the same as stated in the definition of formula I.

Examples of the neutral ester (1) include:
β-hydroxyethyl acrylate and methacrylate methyl β-hydroxyethyl itaconate
2-hydroxypropyl acrylate and methacrylate
3-hydroxypropyl acrylate and methacrylate
2-hydroxy-1-methyl-ethyl acrylate and methacrylate
2-hydroxy-butyl-acrylate and methacrylate
3-hydroxy-butyl-acrylate and methacrylate
4-hydroxy-butyl-acrylate and methacrylate
2-hydroxy-2-methyl-butyl acrylate and methacrylate
2-hydroxyethoxyethyl acrylate and methacrylate
5-hydroxypentyl-acrylate and methacrylate
6-hydroxyhexyl-acrylate and methacrylate
7-hydroxyheptyl-acrylate and methacrylate
4-hydroxy-2-ethyl-butyl acrylate and methacrylate
6-hydroxy-2-ethyl-hexyl acrylate and methacrylate
9-hydroxynonyl acrylate and methacrylate
10-hydroxydecyl acrylate and methacrylate The anhydrides used in the preparation of the sulfoester monomer are the anhydrides of the 1,2-diacid compounds defined by the formula

wherein X is either (1) an aromatic nucleus, such as a benzene or naphthalene ring, substituted in the 2-position by a sulfonic acid group or a carboxylic acid group and optionally in one or more additional positions by one or more sulfonic acid or carboxylic acid groups, or (2) an alkyl group, substituted or unsubstituted, of the formula

wherein R', $R^2$, $R^3$, $R^4$, and $R^5$ are as defined hereinabove.

Examples of the anhydrides (2) include:
o-sulfobenzoic anhydride
4-methyl sulfobenzoic anhydride 4-sulfophthalic anhydride
3,5-disulfophthalic anhydride
4-sulfo-1,8-naphthalic anhydride
sulfosuccinic anhydride
methyl sulfosuccinic anhydride
ethyl sulfosuccinic anhydride
butyl-sulfosuccinic anhydride
sulfopropionic anhydride, i.e., 1,2-oxathiolane-5-one-2,2-dioxide of the formula:

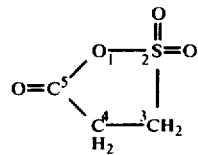

(VI)

4-methyl-1,2-oxathiolane-5-one-2,2-dioxide
4-isobutyl-1,2-oxathiolane-5-one-2,2-dioxide
4-ethyl-1,2-oxathiolane-5-one-2,2-dioxide
3-methyl-1,2-oxathiolane-5-one-2,2-dioxide
3,4-dimethyl-1,2-oxathiolane-5-one-2,2-dioxide The aromatic anhydrides mentioned hereinabove are known compounds. Many of the aliphatic anhydrides listed above are also known. The alkyl-succinic anhydrides are obtained by the reaction of an α-olefin such as ethylene, propylene, butylene or isobutylene with maleic anhydride. The reaction may be carried out in the presence of an inert solvent such as benzene, toluene, and xylene, but a separate solvent is unnecessary if the temperature is high enough to melt the maleic anhydride. Generally, the reaction is effected at a pressure of 25-50 atmospheres which may decrease during the reaction and at a temperature of 150°-250° C. for a period of 8-24 hours. The relative proportions between the reactants may vary widely so that either one may be in excess, an excess of the gas being preferred because of its relative inexpensiveness, but stoichiometric proportions may be used.

The resulting alkyl-succinic acid may then be sulfonated with liquid sulfur trioxide at atmospheric pressure or higher and at room temperature up to 110° C., refluxing if necessary, for a period of about 1-4 hours. The ratio of sulfur trioxide and alkyl-succinic acid employed for the reaction may be stoichiometric or an excess of sulfur trioxide may be used in which case it serves as a solvent.

The oxathiolanes may be produced by the addition of sodium bisulfite (NaHSO₃) to a sodium salt of an appropriate α,β-unsaturated acid. The reaction may be carried out in an aqueous medium at room temperature for 2-12 hours. Generally, it is preferred to employ approximately stoichiometric amounts. The reaction is carried out until the bisulfite ion disappears as indicated by permanganate titration. At the conclusion of the reaction the product is concentrated and converted into the free acid form by ion exchange with a cation exchanger in acid form. The ion exchange resin is filtered off and then the product is stripped and dried. The closure to form the ring is effected in thionyl chloride by heating at temperatures of 60°-80° C. and preferably at reflux for two hours or so. A volatile hydrocarbon solvent, such as ligroin or petroleum ether, is added to precipitate the oxathiolane which then can be separated by filtration or decantation and dried. Unsaturated acids that may be used to form the various oxathiolanes listed above and others include:

acrylic acid
methacrylic acid
crotonic acid
α-methylene-butanoic acid
α-methylene-pentanoic acid
α-methylene-hexanoic acid
2-pentenoic acid
2-hexenoic acid
2-heptenoic acid
α-methyl-crotonic acid
α-ethyl-crotonic acid
α-propyl-crotonic acid
α-butyl-crotonic acid
α-isobutyl-crotonic acid
α-methyl-2-pentenoic acid
α-ethyl-2-pentenoic acid
α-isopropyl-2-pentenoic acid
α-methyl-2-hexenoic acid
α-ethyl-2-hexenoic acid
α-propyl-2-hexenoic acid
α-isobutyl-2-hexenoic acid
α-isopropyl-2-heptenoic acid
2-methylene-4-methyl-pentanoic acid
2-ethylidene-4-methyl-pentanoic acid
2-propylidene-4-methyl pentanoic acid
2-butylidene-4-methyl-pentanoic acid
2-methylene-hexanoic acid
2-butylidene-hexanoic acid The reaction between the unsaturated hydroxyester (1) and the sulfocarboxylic acid anhydride (2) may be carried out under suitable agitation or stirring with a solvent inert to the reactive agents or it may be carried out without a separate solvent. Examples of materials that may be used as solvents include esters, such as ethyl acetate, methyl methacrylate, and butyl acetate, hydrocarbons, such as benzene, toluene, xylene, and ethylbenzene, dimethyl sulfoxide, dioxane, acetonitrile, and so on. The temperature may be from about 0° C. to 130° C. but is preferably in a range from about 20° C. to about 110° C.

The mole ratio of the unsaturated hydroxyester to the sulfocarboxylic anhydride may vary widely. For most practical operations, a ratio is used in the range of 1.5:1 to 1:2 (hydroxyester to anhydride) and the preferred range is from about 1:1 to about 1:1.25.

If it is desired to avoid contamination of the monomeric product with a polymer thereof, a polymerization inhibitor may be used, such as in an amount in the range of about 100 parts per million (ppm) to about 6000 ppm, preferably 1000 to 3000 ppm, based on the weight of the ester. Examples of inhibitors include hydroquinone and the mono- and di-methyl ethers thereof. The time required for the reaction may be from about a half hour to eight hours or more to reach equilibrium conditions. Volatile materials may be removed from the product obtained by vacuum distillation or by extraction with solvents and subsequent distillation of the solvent from the extract.

The sulfonic acid monomer obtained by the reaction is generally obtained in a yield of 70-95% based on the anhydride used assuming approximately equal molar amounts of the hydroxy alkyl acrylate and anhydride are used in the reaction. The monomer of formula I which results from the reaction and is present in acid form in the reaction medium may be directly polymerized with whatever residual content of hydroxyalkyl acrylate or methacrylate monomer is unused in the reaction. However, it may be desirable to isolate either a salt of the sulfonic acid monomer or such monomer in acid form for the purpose of producing homopolymers of such a monomer either in acid or salt form. The sulfo monomer may be isolated from the reaction product by precipitating it with sodium methoxide which forms a salt of the sulfonic acid monomer which is insoluble in whatever organic solvent is used in the preparation of the monomer. Such solvents may be esters, such as ethyl acetate, or hydrocarbons, such as toluene or xylene. After precipitation of the salt of the sulfonic acid monomer, it may be filtered and washed with a solvent such as an ester or an aromatic solvent, ethyl acetate, toluene or xylene being representative of suitable solvents for this purpose. If it is desired to produce a homopolymer of the salt of the monomer thus obtained it may be mixed with a suitable initiator in an aqueous medium. Initiators, such as sodium persulfate, with or without reducing agents such as sodium hydrosulfite, also tertiary-butyl hydroperoxide, hydrogen peroxide or other water-soluble initiator may be used.

If a homopolymer of the sulfonic acid containing monomer is desired the precipitated salt of the monomer which has been filtered and washed as mentioned just above may be suspended in a suitable solvent such as ethyl acetate or toluene and agitated for a period of time with a strong acid ion exchange resin. For example, the suspension of the monomer salt in the organic solvent may be agitated with beads of a sulfonated styrene/divinyl benzene ion exchange resin for a period of several hours at room temperature. The ion exchange resin is initially in the acid form and exchanges the metal ion with the monomer salt and thereby liberates the free acid form of the sulfonic acid containing monomer. As a result of the ion exchange action the monomer is converted to acid form which is soluble in the organic solvent used for suspending the salt form and the ion exchange resin. At that point it is merely necessary to filter off the ion exchange resin.

The acid form of the monomer thereby obtained can then be polymerized, such as in the solution in which it is obtained, by the mere addition of suitable free radical initiators such as azodiisobutyronitrile, diethyl diazodiisobutyrate, benzoyl peroxide or other initiator soluble in the organic solvent.

The acid form of this homopolymer or copolymers obtained from the sulfonic acid monomers of the present invention can be converted essentially entirely or partially to the salt form simply by adding a base, such as an alkali metal hydroxide, alkaline earth metal hydroxide, ammonium hydroxide, or an amine or quaternary ammonium hydroxide. The salt form of the homopolymers or copolymers can also be partially or completely converted to the acid form by leaching the polymers with a strong acid.

The monomeric products obtained, whether or not isolated from the reaction medium are polymerizable to produce homopolymers and/or copolymers, as desired, by bulk, emulsion, solution, and suspension procedures. In general, the monomers of formula I are water-soluble liquids that form water-soluble salts, generally solid and crystalline, with basic material, such as the various bases mentioned hereinabove.

There are many known polymerizable, $\alpha,\beta$-ethylenically unsaturated compounds that can be polymerized while dispersed in aqueous media by means already known per se to produce aqueous colloidal dispersions of substantially water-insoluble solid polymer products. These can be advantageously polymerized in aqueous dispersions that comprise one of the sulfoester monomers of formula I of this invention.

Among such other known polymerizable ethylenically unsaturated compounds are the alkenyl-aromatic compounds, i.e., styrene and o-, m-, and p-vinylstyrene, the derivatives of $\alpha,\beta$-ethylenically unsaturated acids such as the esters, amides, and nitriles of acrylic acid, methacrylic acid, itaconic acid, and maleic acid, unsaturated alcohol esters, unsaturated ketones, unsaturated ethers, and other compounds containing one or more ethylenic linkages, especially those having a single unsaturated group of the formula $H_2C=C<$, capable of addition polymerization. Specific examples of such ethylenically unsaturated compounds are styrene, $\alpha$-methylstyrene, ar-methylstyrene, ar-ethylstyrene, $\alpha$,ar-dimethylstyrene, ar,ar-dimethylstyrene, vinylnaphthalene, hydroxystyrene, methoxystyrene, cyanostyrene, acetylstyrene, monochlorostyrene, dichlorostyrene and other halostyrenes, methyl methacrylate, ethyl acrylate, butyl acrylate, butyl methacrylate, hexyl acrylate, lauryl methacrylate, phenyl acrylate, acrylonitrile, methacrylonitrile, acrylanilide, acrylamide, N-methylolacrylamide, ethyl $\alpha$-chloroacrylate, ethyl maleate, polyglycol maleate, vinyl acetate, vinyl propionate, vinyl butyrate, vinyl benzoate, vinyl chloride, vinyl bromide, vinylidene chloride, vinylidene bromide, vinyl methyl ketone, isopropenyl ketone, vinyl ethyl ether, and dienes which generally act as though they have only one point of unsaturation during normal polymerization, such as 1,3-butadiene, isoprene, and the like.

The monomers of formula I and their water-soluble salts may be homopolymerized in bulk or in an aqueous solution thereof using a suitable polymerization catalyst or initiator or an initiator system, such as a redox system. The catalyst or initiator may simply be radiation, especially ultra-violet light, or it may be a free radical type of initiator, miscible with the monomer or soluble in the aqueous medium. Examples include hydrogen peroxide, ammonium or an alkali metal (e.g. sodium or potassium) persulfate, t-butyl hydroperoxide, cumene hydroperoxide or azo-bisisobutyronitrile. Such initiators may be used in the customary amounts of about 0.1 to 3% by weight based on total monomer weight. In redox systems, a free radical initiator, such as the type mentioned is used with a reducing agent, such as sodium hydrosulfite, potassium metabisulfite, or ascorbic acid, in comparable amounts, e.g. 0.1 to 3% based on monomer weight. Any suitable pH may be maintained such as in the range from 3 to 10, an acid, base, and/or buffering agent or agents being included as desired.

Homopolymers and copolymers can also be produced in any other solvent medium, such as an ester, e.g. ethyl acetate, a ketone, e.g., acetone or methyl isobutyl ketone, an ether, e.g. dioxane, and the dimethyl ether of diethylene glycol, or mixtures containing two or more such solvents or containing water and one or more of the organic solvents just mentioned. Alcohols are unsuitable for use as the solvent medium whenever complex ester product mixtures are to be avoided. An initiator or initiator system that is soluble in the medium may be used, such as any of those mentioned above for use in the aqueous systems.

Copolymers of one or more other monomers, such as those previously mentioned, with a monomer of formula I can be produced efficiently in an aqueous medium, with or without the use of an emulsifying agent to aid in the dispersion of any water-insoluble monomer. When an emulsifier is used, it may be used in conventional amount in the range of 0.05 to 6% or more based on the weight of water-insoluble monomer used in the polymerization process. The water-soluble initiator or initiator systems mentioned above may be used in the amounts stated. Generally, the polymers produced have high molecular weight, such as from about one million to ten millions or more. However, a chain transfer agent, such s bromotrichloroethane, methylene chloride, a ($C_2$-$C_{12}$)alkyl mercaptan, e.g. dodecyl mercaptan, or a hydroxyalkyl mercaptan, e.g. $\beta$-hydroxyethyl mercaptan, may be used to obtain polymers of lower molecular weights, such as from about 10,000 to any point below that which the system in use normally produces without such an agent, the more of the agent used, the lower the molecular weight for any particular chain transfer agent. The amount of such an agent used may be from about 0.05% to 10% or more based on the total monomer weight.

A suspension polymerization technique of normal type employing a colloid, such as polyacrylic acid or poly($\alpha$-vinylpyrrolidinone), may be used to form copolymers containing a large proportion of at least one monomer of formula I cross-linked by about to 5 to 50% (preferably 15 to 35%) by weight of a diethylenically unsaturated copolymerizable monomer such as divinyl benzene, ethylene glycol dimethacrylate, or diallyl phthalate. Such polymers are obtained in the form of beads or granules which are useful as cation-exchange resins.

The monomers of formula I as well as the homopolymers of a monomer of formula I herein and copolymers formed largely (at least 55% by weight) of one or more monomers of formula I and containing 0% to 45% by weight of other monomers of the types mentioned hereinabove are useful as surfactants, such as wetting agents, as antistatic agents for textiles and other articles formed of hydrophobic materials such as nylon, cellulose esters, and polyesters and as softening agents for textiles, such as cotton and rayon. They are also useful as conductivity aids in paper, such as that used in electrostatic reproduction. They are also useful to stabilize aqueous polymer dispersions and water-base paints against coagulation as a result of freezing and subsequent thawing. They, and especially the polymers, are useful as flocculating agents. To serve these purposes, the amount of the monomer or polymer needed is quite small relative to the magnitude of the system to which or in which they are applied.

When a relatively small amount of a monomer of formula I is incorporated as a polymerized component in water-insoluble polymers used in the coatings industry, the copolymers that are obtained show remarkable improvements in adhesion to various substrates, and especially those of, or carrying a deposit of, a plastic or resinous material.

The polymers contemplated here are the addition polymers of at least one monoethylenically unsaturated monomer having a group of the formula $H_2C=C<$, including a vinyl ester of a ($C_1$-$C_{18}$)alkanoic acid, e.g. vinyl acetate, vinyl versatate, and vinyl dodecanoate; a ($C_1$-$C_{18}$)alkyl ester of acrylic acid or methacrylic acid, such as methyl acrylate, methyl methacrylate, ethyl acrylate, ethyl methacrylate, butyl acrylate, butyl methacrylate, 2-ethylhexyl acrylate or methacrylate; a vinylaromatic hydrocarbon, such as styrene and vinyltoluene; acrylonitrile, acrylamide and so forth.

Thus the copolymers containing from as little as 0.1% by weight, based on copolymer weight, up to 2% or 5% by weight of a monomer of formula I are exceptionally useful for improving the adhesion of coatings of compositions comprising such copolymers when applied to substrates of metal, glass, or plastic carrying a deposit of a vic-epoxy resin primer, an aminoplast resin primer, or primers formed of mixtures of such resin-forming substances, all of which are of commercial types commonly available on the market.

Copolymers of monoethylenically unsaturated compounds containing small amounts of a monomer of formula I such as from about 0.2% to 5% or even up to 10% are useful to impart antistatic properties to textiles and other materials formed of hydrophobic materials, such as nylon, cellulose esters including cellulose acetate and cellulose acetate butyrate, and polymers such as the condensates of ethylene glycol with terephthalic acid. Preferably, such copolymers are prepared by emulsion polymerization processes so that a latex or aqueous dispersion of the polymer is produced containing anywhere from 20 to 60% by weight of the polymer dispersed therein. In applying the dispersion to the fabric or other material the dispersion may be diluted to about 15 to 30% solids and applied by spraying, use of a textile pad, or brushing as is most suitable for application to the particular substrate involved. Effective antistatic properties are obtained by the application of an amount from about 0.1 to 14% by weight of the polymer based on the weight of fibers in the case of the textile material whereas effective antistatic property is obtained by the application of such a polymer on a solid article such as a molded plastic article when the polymer is deposited in the form of a thin film of about 1–10 microns thickness.

In the preferred monomers there is a carboxylic acid group as well as the sulfonic acid group or groups. There is an advantage in having carboxyl groups in addition to the sulfonic acid groups. The presence of the carboxyl group is particularly important in aqueous polymer dispersions made from the polymers containing small amounts, such as 0.2 to 5% by weight, of a monomer of formula I in that such dispersions and compositions made therefrom, such as water base paints, can readily be thickened by the addition of a basic material such as sodium hydroxide, ammonium hydroxide or an amine. This amenability to thickening by adjustment of the pH of the system when such a basic material is added provides an efficient way of controlling the viscosity and consistency of the products to adapt them for any particular manner of application for use as in brushing, spraying or the like.

Another remarkable property that is clearly enhanced by the presence of carboxyl groups in the polymers is the dispersing action of such polymers for fillers, pigments, delustrants and other inert materials. The dispersancy improvement occurs not only in aqueous dispersions of the polymers containing the monomers of formula I when it contains carboxyl groups but also is found to occur in organic solvent systems containing such polymer dissolved therein or dispersed therein in the form of a non-aqueous dispersion. While these advantages i.e., amenability to thickening and improvement of dispersing action can be obtained when the polymer is made from a monomer of formula I lacking carboxylic acid groups by the inclusion of separate carboxylic acid monomers such as acrylic acid, methacrylic acid and itaconic acid in small amounts such as from 0.2 to 5% by weight in the polymer, nevertheless, it has generally been found that the inclusion of the carboxylic acid groups in the sulfoester monomer of formula I is more practical and efficient as well as somewhat more economical. Thus the preferred monomers that incorporate both sulfonic acid and carboxylic acid groups (in free acid or salt form) provide outstanding qualities in compositions such as water base paints made therefrom.

While the polymers of the invention hereinabove described are produced directly by polymerization of a monomer of formula I, another avenue to produce polymers of the present invention is to polymerize a hydroxyl-containing ester monomer of formula IV and after production of the polymer reacting it with an anhydride of a compound of formula V at a temperature of. The polymerization of the hydroxyl-containing compound is well known in the art and the reaction with the anhydride can be carried out under essentially the same conditions as are specified hereinabove in the description of the procedure for reacting such an anhydride with such a hydroxy ester in making the monomers of formula I.

To assist those skilled in the art to practice the present invention, the following modes of operation are suggested by way of illustration, parts and percentages being by weight and the temperature in ° C. unless otherwise specifically noted.

(A) PREPARATION OF 4-SULFOPHTHALIC ANHYDRIDE

Phthalic anhydride (148 grams) and chlorosulfonic acid (116.5 grams) are mixed in a reaction flask fitted with a condenser, stirrer and thermometer. The reaction temperature is raised to 225° C. over a period of about 14 hours. After a further 2 hours at this temperature, g.l.c. analysis indicates that the reaction mixture still contains 10% by weight of phthalic anhydride. At about 23 hours total reaction phthalic anhydride is no longer detectable. The resulting product is cooled to 160° C. and stripped for 30 min. at 20 mm Hg to remove residual hydrogen chloride. Cooling to room temperature affords a viscous red liquid having infrared (i.r.) spectral data and equivalent weight (76) consistent with 4-sulfophthalic anhydride.

(B) PREPARATION OF SULFONIC ACID MONOMERS:

(1) PREPARATION OF METHACRYLOXYISOPROPYL ACID SULFOPHTHALATE:

(a) A mixture of 239 g. 4-sulfophthalic anhydride (1.05M), 151 g. 2-hydroxypropyl methacrylate (1.05M), 260 g. methyl methacrylate (2.6M) as solvent, and the monomethyl ether of hydroquinone (0.25g.) is charged to a reactor fitted with a condenser, thermometer, stirrer, and an air-sparge tube. The stirrer is operated continuously and dry air is passed through the tube at a rate of about 300 ml./min. After 2 hours at 60° C. the product is cooled to room temperature. Analysis indicates that the equilibrium mixture contains about 55% by weight methacryloxyisopropyl acid sulfophthalate.

The mixture obtained can be used directly for polymerization but it may be desirable to purify the monomer as follows: Add sodium methoxide in sufficient quantity to precipitate the sodium salt of the sulfonic acid monomer. Then filter and wash with ethyl acrylate or xylene. This monomer salt can be homopolymerized by adding it to water and then adding a polymerization initiator. The example, add 100 g. of the monomer salt to 180 g. of water. Then add 0.9 g. sodium persulfate. The mixture is maintained at 50° C. to 60° C. until the reaction subsides as evidenced by reduction in temperature.

(b) The homopolymer salt thus obtained in part (a) is useful as a polymeric electrolyte. For example, it serves as a suspending agent in a suspension polymerization as follows: A 1% solution of this polymer salt in a liter of water is heated to 50° C. with agitation. Then, while continuing the stirring, a mixture of 400 g. of styrene, 100 g. of divinylbenzene and 4 g. of benzoyl peroxide is added over a period of 6 hours while maintaining the temperature so that it does not exceed 85° C. The styrene/divinylbenzene copolymer precipitates as small beads which, on sulfonation in conventional manner, are converted into a strong acid ion-exchange resin.

(c) The filtered and washed monomer salt obtained in part a) (50 g.) is stirred in 200 g. ethyl acetate and 75 g. of a granular sulfonated styrene/divinylbenzene ion-exchange resin in acid form is stirred in. The resulting mixture is stirred continuously for a period of four hours at room temperature. The monomer as it is converted to acid form dissolves in the solvent. The resulting slurry is then filtered yielding a filtrate containing approximately 23% of the methacryloxyisopropyl acid sulfophthalate. About 1.5 g. of lauroyl peroxide is added to the solution and the temperature then rises to about 65° C. After an hour of polymerization, the temperature falls. Cotton and viscose yarns are passed through the polymer solution after dilution to about 5% concentration with additional ethyl acetate. The yarns are then heated to evaporate the solvent in a suitable evacuation chamber. The yarns are thereby sized for protection during textile operations, such as weaving or knitting. After the latter operations, the size is removed by passage of the fabric through an alkaline bath.

(d) In a similar fashion to that described in part a) methacryloxyisopropyl acid sulfophthalate is obtained as a 55% solution in ethyl acetate. It is converted to the sodium salt in the same way as described in part a) hereof.

2) PREPARATION OF METHACRYLOXYISOPROPYL SULFOBENZOATE:

(a) 54.7 g. 2-hydroxypropyl methacrylate (0.38M), 70 g. o-sulfobenzoic anhydride (0.38M) and the monomethyl ether of hydroquinone (0.1 g.) are dissolved in toluene (35 g.) and heated to 110° C. The mixture is agitated and sparged with dry air as in 1) above. After 2 hours, the reaction mixture is cooled and analysis shows that methacryloxyisopropyl sulfobenzoate is obtained in approximately 75% yield based on o-sulfobenzoic anhydride charged.

(b) To the resulting solution of methacryloxyisopropylsulfobenzoate in toluene there is added sodium methoxide to effect precipitation of the salt of the monomer. The precipitated salt is filtered and rinsed with additional toluene. The salt is polymerized in the same way as the filtered and washed monomer salt obtained in 1)a) above. The resulting polymer is used as a suspending agent in a suspension polymerization in the same way as is described in procedure 1)b) above.

(c) The filtered salt of the methacryloxyisopropyl sulfobenzoate is converted to the acid form in the same way as described in 1)c) above. The resulting monomeric acid is polymerized in the same way as described in part 1)c) and is applied for the sizing of warp yarns in the same way as therein described. As in the previous instance, the size is readily removable in an aqueous alkaline solution.

(3) PREPARATION OF METHACRYLOXYISOPROPYL ACID SULFOSUCCINATE:

Into a reaction flask fitted with a thermometer, stirrer, condenser, and an air-bleed tube, there is charged 21.8 g. potassium sulfosuccinic anhydride (0.1M), 14.4 g. 2-hydroxypropyl methacrylate (0.1M), dimethyl sulfoxide (34 g.) and the monomethyl ether of hydroquinone (0.02 g.). The reactants are agitated and sparged with air as in 1) and they are heated to 100° C. for 6 hours and then cooled to room temperature. A calculated quantity of a sulfonated styrene/divinyl benzene ion-exchange resin is added and stirring is continued at 25° C. for 16 hours. After filtering to remove the ion-exchange resin, a 40% by weight solution of methacryloxyisopropyl acid sulfosuccinate in dimethyl sulfoxide is obtained.

The resulting monomer is polymerized by adding benzoyl peroxide (1 gram thereof per 100 grams of monomer) to the solution thereof and maintaining it at a temperature of about 60° C. for several hours. Cotton and rayon yarns are sized in the resulting solution of polymeric acid, the solvent being evaporated after application to the yarns. The sized yarns are fabricated into textile fabrics and thereafter the fabrics are immersed in an aqueous alkaline medium such as 1% sodium hydroxide solution to remove the size from the fabric.

(4) PREPARATION OF METHACRYLOXYETHYL SULFOBENZOATE

Hydroxyethyl methacrylate (65 g.), o-sulfobenzoic anhydride (92 g.), the monomethyl ether of hydroquinone (0.2 g.) and toluene (157 g.) are stirred, sparged with dry air, and heated at 110° C. for 2 hours and then cooled to room temperature. Analysis indicates an approximately 74% conversion of anhydride into methacryloxyethyl sulfobenzoate.

The resulting monomer may be converted, by salting out, into the salt which can be polymerized in the fashion described hereinabove or the monomeric salt may be converted back to the acid form of the monomer by use of ion exchange resins as described hereinabove and the resulting solution of the acid form of the monomer may be polymerized to form a polymer which is a suitable size for textile yarns that is readily removable after fabrication of the yarns into a textile fabric by means of an alkaline medium.

(5) PREPARATION OF METHACRYLOXYISOPROPYL SULFOPROPIONATE:

To a reaction vessel fitted with an air-bleed tube, thermometer, stirrer, and condenser there are charged sulfopropionic anhydride (29.1 g.), 2-hydroxypropyl methacrylate (29.1 g.), the monomethyl ether of hydroquinone (0.1 g.) and toluene (60 g.). The mixture is stirred, sparged with dry air as in 1) above and heated. After 0.5 hour at 60° C. a solution containing 29% by weight of methacryloxyisopropyl sulfopropionate is obtained.

(6) PREPARATION OF METHACRYLOXYISOPROPYL ACID SULFOPHTHALATE:

(a) A mixture of 228 parts of 4-sulfophthalic anhydride (1.0M), 144 parts of hydroxypropyl methacrylate (1.0M), 260 parts of methyl methacrylate (2.6M) as solvent, and the monomethyl ether of hydroquinone (0.25 parts) is charged to a reactor fitted with a condenser, thermometer, stirrer and air-sparge tube. A slow stream of dry air is passed through the solution while maintaining a temperature of 60° C. by the application of external heating. After 2 hours the product is cooled to room temperature and analyzed. The product contains approximately 53% by weight of methacryloxyisopropyl acid sulfophthate.

(b) Substituting 129.8 parts of hydroxypropyl methacrylate for the 144 parts used in 6)a) above, yields a product containing approximately 50% wt. methacryloxyisopropyl acid sulfophthalate.

(7) PREPARATION OF METHACRYLOXYETHYL ACID SULFO-METHYL-SUCCINATE:

(a) A mixture of 194 g. of sulfo-methyl-succinic anhydride, 130 g. of β-hydroxyethyl methacrylate, 280 g. of methyl methacrylate and 0.3 g. of the monomethyl ether of hydroquinone is charged to a reaction vessel. The mixture is continuously stirred and dry air is passed through the solution at a rate of 200 ml./min. The mixture is heated 2 hours at 60° C. and then cooled to room temperature. The product may also be named the mono(β-methacryloxyethyl) ester of sulfo-methyl-succinic acid.

(b) PREPARATION OF SULFO-METHYL-SUCCINIC ANHYDRIDE:

114 g. of methyl-succinic anhydride and 80 g. of liquid sulfur trioxide are stirred and heated to 110° C. in an apparatus fitted with a condenser adequate to contain the low boiling sulfur trioxide. After 1 hour, the product is cooled to 25° C. and has an equivalent weight of about 65. It is stored as a solution in methyl methacrylate.

(c) The methacryloxyethyl acid methyl-sulfo-succinate obtained in part a) hereof can be used directly for polymerization or it may be precipitated from solution by the addition of sodium methoxide. The salt can be homopolymerized as described previously or it may be converted into the free acid monomer prior to polymerization by the procedure described using a cation exchange resin in acid form.

(8) (a) PREPARATION OF METHACRYLOXYETHYL ACID n-BUTYL-SULFO-SUCCINATE:

This product is obtained from β-hydroxyethyl methacrylate and n-butyl-sulfo-succinic acid anhydride by the procedure of 7)a) using corresponding molar amounts of the reactants. The anhydride is obtained as follows:

(b) 30 g. of maleic anhydride and 40 g. of butene-1 are dissolved in 40 g. benzene in an autoclave. After 8 hours' heating at 250° C. a pressure drop from 40 to 2 atmospheres is noted and the reaction is terminated. The brown solution obtained is vacuum-distilled to yield 40 g. of butenylsuccinic anhydride, boiling range 144°–147° C. at 4 mm Hg pressure, characterized as the free acid m.p. 114° C., literature 114°–115° C.

40 g. of the butenylsuccinic acid is hydrogenated in methanol over a platinum catalyst to yield n-butylsuccinic acid, m.p. 82°–83° C. Ring closure to n-butyl-succinic anhydride is achieved by mixing it with 100 g. of acetic anhydride and distilling acetic acid as it is formed. The resulting crude product is directly sulfonated by the procedure of 7)b) using corresponding molar amounts of the n-butyl-succinic anhydride and $SO_3$.

(9) PREPARATION OF METHACRYLOXYISOPROPYL SULFO-ISOBUTYRATE:

(a) 150 g. of 4-methyl-1,2-oxathiolane-5-one-2,2-dioxide prepared as described in part b) hereof, 144 g. of β-hydroxypropyl methacrylate, 0.2 g. of the monomethyl ether of hydroquinone and 200 g. of toluene are heated at 60° C. with stirring and air sparging with 200 ml/min. of dry air for 1 hr. The cooled mixture contains a 75% yield of methacryloxyisopropyl sulfo-isobutyrate.

(b) PREPARATION OF 4-METHYL-1,2-OXATHIOLANE-5-ONE-2,2-DIOXIDE:

88 g. of isobutyric acid dissolved in 100 g. of sulfuryl chloride is heated at 80° C. and irradiated with a 300 watt tungsten lamp for 2 hours. Addition of ligroin precipitates an oil which has a boiling range 135°–140° at 4mm and is identified as 4-methyl-1,2-oxathiolane-5-one-2,2-dioxide by its equivalent weight, 75.

(10) PREPARATION OF METHACRYLOXYISOPROPYL β-SULFO-HEXANOATE:

(a) 178 g. of 3-propyl-1,2-oxathiolane-5-one-2,2-dioxide is reacted with 144 g. of β-hydroxypropyl methacrylate in toluene as described in procedure 7)a) above.

(b) PREPARATION OF 3-n-PROPYL-1,2-OXATHIOLANE-5-ONE-2,2-DIOXIDE:

114 g. of 2-hexenoic acid is neutralized with aqueous sodium hydroxide and reacted with 204 g. of a 50% wt. aqueous solution of sodium bisulfite at 25° C. Complete addition of bisulfite to the double bond requires several hours. The product is concentrated to approximately 50% wt. solids and then treated with a strong acid ion exchange resin to obtain an aqueous solution of 3-sulfohexanoic acid. This is dried by vacuum stripping and converted into 3-propyl-1,2-oxathiolane-5-one-2,2-dioxide with refluxing thionyl chloride at 80° C. for 3 hours. Equivalent weight is 93.

(11) PREPARATION OF METHACRYLOXYISOPROPYL 2-(SULFOMETHYL)-PENTANOATE:

(a) 178 g. of 4-n-propyl-1,2-oxathiolane-5-one 2,2-dioxide and β-hydroxypropyl methacrylate are reacted in toluene as described in procedure 7)a) above to produce methacryloxyisopropyl 2-(sulfomethyl)-pentanoate.

(b) PREPARATION OF 4-n-PROPYL-1,2-OXATHIOLANE-5-ONE-2,2-DIOXIDE:

114 g. of α-methylene-pentanoic acid is reacted with sodium hydroxide to neutralize the carboxyl group. Sodium bisulfite (1 mol) solution is added and the reaction carried out as described in procedure 10)b) to obtain 4-n-propyl-1,2-oxathiolane-5-one-2,2-dioxide of an equivalent weight of 93.

(12) By procedure 7)a) above, β-hydroxyethyl methacrylate is esterified with an equimolar amount of allyl-sulfo-succinic anhydride obtained by the sulfonation of allyl-succinic acid anhydride obtained from propene and maleic anhydride by a procedure analogous to that of 8)b) hereinabove.

(13) PREPARATION OF METHACRYLOXYETHYL 2-METHYL-3-SULFO-BUTYRATE:

By procedure 9)a) above, β-hydroxyethyl methacrylate is reacted with an equimolar amount of 3,4-dimethyl-1,2-oxathiolane-5-one-2,2-dioxide. There is obtained a 70% yield of methacryloxyethyl-2-methyl-3-sulfo-butyrate.

The thiolane used is obtained as follows:

100 g. of α-methyl-crotonic acid is reacted with sodium hydroxide to neutralize the carboxyl group. Sodium bisulfite (104 g.) in aqueous solution is added and the reaction continued as described in earlier examples to obtain 3,4-dimethyl-1,2-oxathiolane-5-one-2,2-dioxide.

The reaction of this product with hydroxymethyl acrylate and methacrylate is as described in earlier examples to give e.g. methacryloxyisopropyl-α-methyl-β-sulfobutanoate.

(14) CORRESPONDING ACRYLOXYALKYL SULFO-CONTAINING MONOMERS:

Each of the preceding procedures in which a methacryloxy-containing compound of the present invention is produced is repeated with the replacement of the hydroxyalkyl methacrylate by the corresponding molar amount of a hydroxyalkyl acrylate, thereby producing the corresponding acryloxy-containing monomer.

For example, acryloxyisopropyl acid sulfophthalate is produced by mixing 239 grams of 4-sulfophthalic anhydride (1.05M), 136 grams of 2-hydroxypropyl acrylate (1.05M), 260 g. methyl methacrylate (as solvent) and 0.25 grams of monomethyl ether of hydroquinone in a reactor which is continuously stirred and sparged with dry air. After 2 hours at 60° C. the product is cooled to room temperature and contains about 50% by weight of acryloxyisopropyl acid sulfophthalate.

This monomer can be isolated from the methyl methacrylate by precipitating out a salt and then by filtration. The monomer salt is then polymerized and used as a suspending agent in the same suspension polymerization procedure as is disclosed in 1)b). Furthermore, the filtered and washed monomer salt is converted to the monomer acid by slurrying the salt in ethyl acetate and stirring with a sulfonated styrene/divinyl benzene ion exchange resin in acid form. The acid monomer is then obtained in solution by filtration and polymerized by the addition of 1% benzoyl peroxide. It is useful for the sizing of cotton and rayon yarns which, after fabricated, can be treated with an aqueous alkaline solution to remove the size therefrom.

(15) PREPARATION OF ACRYLOXYETHYL ACID SULFOPHTHALATE:

Hydroxyethyl acrylate (130 g.), 4-sulfophthalic anhydride (227 g.), butylacetate (250 g.) and monoethylether of hydroquinone (0.25 g.) are mixed, stirred, sparged with dry air and heated at 105° C. for 3 hours and cooled.

(C) PREPARATION AND USE OF POLYMERS:

(1) 400 parts of methyl methacrylate and 1 part of azodiisobutyronitrile are added in the course of one hour to a glass reaction vessel containing 287.5 parts of toluene maintained at 80° C. by means of external heating. The mixture in the flask is stirred during the addition and subsequent reaction and maintained at 80°-85° C. under a nitrogen atmosphere. The mixture is then diluted with 332.5 parts of toluene over one hour while stirring and maintaining the temperature at 80°-82° C. At the end of two hours (about 90% conversion), a second stage comprised of 95.0 parts of methyl methacrylate and 5.0 parts of methacryloxyisopropyl acid sulfophthalate, 0.25 parts of azodiisobutyronitrile, and 25 parts of 2-methoxyethanol is added in the course of one hour to the same reaction vessel using the heated methyl methacrylate resin solution as the reaction medium. Stirring and heating are continued and a reaction temperature of 80°-82° C. maintained. After 5 hours the mixture is again diluted with an additional 25 parts of toluene over a one-hour period. Four, six and eight hours after initial polymerization has started the overall reaction is recatalyzed with 0.1 part of additional azodiisobutyronitrile. Heating and stirring are continued for a total of 12 hours and the mixture diluted with toluene to 30% solids. (approx. 418.3 parts of toluene). The final Gardner-Holdt viscosity is Q. The final product, a clear viscous liquid, contains a copolymer of 99 parts of methyl methacrylate and 1.0 part of methacryloxyisopropyl acid sulfophthalate.

Coatings are made on panels of metal primed with an acrylic polymer/melamine formaldehyde primer. Adhesion to such panels is excellent; coatings of poly(methyl methacrylate) lack such adhesion. Similar copolymers containing 2% of the methacryloxyisopropyl acid sulfophthalate show even stronger adhesion to various substrates including conventional metal primer coatings such as those based on alkyds, epoxide resins, aminoplasts, and mixtures thereof.

(2)a) The procedure described in C)1) is repeated substituting for the initial monomer charge 278.8 parts of methyl methacrylate, 119.6 parts of ethyl acrylate and 1.6 parts of methacrylic acid, and also substituting for the second charge 264.8 parts of methyl methacrylate, 113.6 parts of ethyl acrylate, 2.0 parts of methacryloxyisopropyl acid sulfophthalate and 1.6 parts of methacrylic acid, 1.0 part of azodiisobutyronitrile, and 100 parts of 2-methoxyethanol. The resulting composition, when diluted to 40% solid with toluene, is a clear polymer solution having a viscosity of Z-5.

(b) Part a) hereof is repeated using 2.0 parts of acryloxyisopropyl acid sulfophthalate instead of the corresponding methacryloxy compound.

The clear solutions of parts a) and b) hereof are applied to various substrates and dried. The coatings have good gloss, clarity and adhesion on panels of various metals.

(3) The procedure described in C)2) is repeated substituting methacryloxyisopropyl sulfobenzoate for methacryloxyisopropyl acid sulfophthalate. The final polymer solution at 40% resin solids has a viscosity of Z.

(4) 76.25 parts of methacryloxyisopropyl acid sulfophthalate and 1 part of azodiisobutyronitrile dissolved in 48.75 parts of n-butyl acetate are maintained at 120° C. by means of external heating. The mixture is stirred for 5 hours and the reaction kept under a nitrogen atmosphere. The final 60% solids polymer solution has a viscosity of 500 cps.

(5) A mixture comprising 39.25 parts of methyl methacrylate, 45.1 parts of butyl acrylate, 3.3 parts of methacryloxyisopropyl acid sulfophthalate, 7 parts of methyl Cellosolve, 4.35 parts of toluene, and 0.09 parts of benzoyl peroxide is diluted in a glass reaction vessel with 186.3 parts of toluene. The reaction flask is maintained under an atmosphere of nitrogen and external heating applied to raise the temperature to 110° C. At reflux a mixture comprising 117.75 parts of methyl methacrylate, 135.3 parts of butyl acrylate, 9.9 parts of methacryloxyisopropyl acid sulfophthalate, 21 parts of methyl Cellosolve, 13 parts of toluene, and 0.27 parts of benzoyl peroxide is added over a period of two hours maintaining reflux by external heating and maintaining the nitrogen atmosphere in the reaction flask. After this addition, reinitiation is effected by a one-hour addition of 1.58 parts of benzyol peroxide dissolved in 118.3 parts of toluene. At 25° C. the resulting light brown polymer solution has a viscosity of 4970 cps. at 48.8% resin solids.

(6)a) A polymer similar to that described in C)5) is prepared with methacryloxyisopropyl sulfopropionate substituted for methacryloxyisopropyl acid sulfophthalate. The product has a viscosity of 4000 cps. at 50% polymer solids.

(b) A polymer similar to that described in C)5) is prepared with methacryloxyethyl acid sulfophthalate substituted for methacryloxyisopropyl acid sulfophthalate. The product has a viscosity of 4000 cps. at 50% polymer solids.

The polymer solutions of C)3), 4), 5) and 6)b) are used for coating various substrates, especially metals primed with various commercial primers. The solutions may be so applied to provide clear protective coats on drying or they may be formulated with pigments, such as $TiO_2$ before application. For example, a solution of a respective one of the polymers is diluted to about 15% polymer solids and 100 parts of this diluted solution is mixed with about 12 parts of $TiO_2$ in a suitable mill. The clear, as well as the $TiO_2$- pigmented lacquers, exhibit viscosity stability over a reasonably long storage time, such as is evidenced by an accelerated storage test over a period of 72 hours at 140° F.

(7) A mixture of 24 parts of a 28% aqueous solution of sodium octylphenoxydiethoxyethyl sulfonate in 376 parts of water is placed in a vessel equipped with stirrer, condenser, gas inlet, and thermometer. After purging with nitrogen, the following ingredients are added: 15.6 parts of a 55% solution methacryloxyisopropyl acid sulfophthalate in methyl methacrylate, 100 parts of butyl acrylate, 85.2 parts of methyl methacrylate, 20 parts of a 0.15% aqueous solution of ferrous sulfate heptahydrate, and a solution of 1 part of ammonium persulfate in 5 parts of water. After stirring for 15 minutes, the batch is cooled to 25° C. and a solution of 0.7 parts of sodium formaldehyde sulfoxylate in 5 parts of water is added followed by 0.12 parts of 70% t-butyl hydroperoxide. Polymerization begins immediately, and the temperature rises to 66° C. in 7 minutes. The batch is held at 66° C. for 15 minutes, cooled and filtered through cheese cloth. A negligible quantity of gum is formed; a stable latex is obtained with a solids content of 32.1% and a pH of 1.7.

(8) Procedure C)7) is repeated except that the methacryloxyisopropyl acid sulfophthalate is replaced by the corresponding amount of each of the following monomers:

(a) acryloxyethyl acid sulfophthalate
(b) methacryloxyisopropyl sulfobenzoate
(c) methacryloxyethyl sulfobenzoate (9) There are mixed and ground on a roller mill 266.2 parts of titanium dioxide, 76.0 parts of lithopone, 51.5 parts of mica, 80 7 parts of silica, 6.8 parts of the formaldehyde-condensed sodium naphthalene sulfonate, 7.2 parts of diethylene glycol, and 189.5 parts of water. When this mixture has been ground to a smooth, uniform paste, it is mixed with 258 parts of a dispersion of interpolymer, which contains 32% solids and which has been prepared as in C)7) above. When the parts used are pounds, this formula yields 100 gallons of a white flat paint. It weighs 11.96 pounds per gallon, contains 59.6% of non-volatile matter, has a pigment to binder ratio of 2:1, and has a pigment volume concentration of 36%.

The resulting water-base paint provides coatings on a wide variety of substrates, such as masonry, plaster, wood, metals, and various plastic materials which coatings show good to excellent adhesion to most if not all, such as steel, galvanized iron, aluminum and copper, of these surfaces under normal conditions of use:

(10) Each of the polymer dispersions of C)8)a), b), and c) are formulated into water-base paints in the same way as described in 9) immediately above. Coatings have similar qualities of adhesion and durability as those obtained from the paint made in 9) above.

(1) Procedure C)1) is repeated with similar results substituting for the methacryloxyisopropyl acid sulfophthalate each of the following monomers respectively:

(a) Methacryloxyethyl acid sulfo-(n-propyl)-succinate
(b) Methacryloxyethyl acid sulfo-(methyl)-succinate
(c) Methacryloxyethyl acid sulfo-(n-butyl)-succinic
(d) Methacryloxyethyl sulfo-(2,3-dimethyl)-propionate
(e) Methacryloxyisopropyl β-sulfohexanoate
(f) Methacryloxyisopropyl 2-(sulfomethyl)-pentanoate

We claim:

1. An addition copolymer of a compound, and salts thereof, of the formula:

$$H_2C=C(R)-\overset{O}{\underset{\|}{C}}-O-A-O-\overset{O}{\underset{\|}{C}}-X \quad (I)$$

wherein
R is hydrogen or methyl,
A is an alkylene group having 2 to 10 carbon atoms, at least 2 of which extend in a chain between the adjoined oxygen atoms, and
X is selected from the group consisting of (a) a benzene ring substituted by at least one sulfonic acid group, (b) a benzene ring substituted by at least one sulfonic acid group and at least one carboxylic group, and (c) an alkyl group of the formula

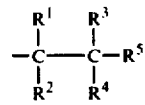

wherein on of $R^1$ and $R^3$ is a sulfonic acid group and the other is H,
$R^2$ is selected from the group consisting of H and $(C_1-C_4)$alkyl groups,
$R^4$ is selected from the group consisting of H, —COOH, and $(C_1-C_4)$alkyl groups, and
$R^5$ is selected from the group consisting of H and $(C_1-C_4)$alkyl groups, with the proviso that only one of $R^2$, $R^4$ and $R^5$ is alkyl, except that both $R^2$ and $R^4$ may be alkyl, provided that $R^1$ and $R^5$ are both H, with at least one other copolymerizable ethylenically unsaturated monomer, and in which the monomer of Formula I is present in an amount of about 0.1% to 10% by weight of the total monomers.

2. A copolymer according to claim 1 wherein X is (a).
3. A copolymer according to claim 1 wherein X is (b).
4. A copolymer is accordance with claim 1 wherein X is (c).
5. A copolymer according to claim 3 wherein the monomer of Formula I is p-sulfo-substituted mono-(methacryloxyisopropyl)ester of o-phthalic acid.
6. A copolymer in accordance with claim 1 of the monomer of Formula I with at least one monomer having a group of the formula $H_2C=C<$.
7. The copolymer of claim 1 in which the monomer of Formula I is copolymerized with at least one different monomer in the form of an α,β-ethylenically unsaturated acid; an ester, amide or nitrile thereof; an unsaturated alcohol ester of a carboxylic acid; an unsaturated ketone or ether; an alkenyl aromatic compound; or a diene.
8. The copolymer of claim 7 in the form of a latex polymer, a suspension polymer, a solution polymer, or a bulk polymer.
9. A substrate having a coating thereon containing the copolymer of claim 7.
10. A lacquer or paint containing the copolymer of claim 7.
11. A water based paint containing the copolymer of claim 7.
12. The copolymer of claim 7 in which the monomer of Formula I is p-sulfo-substituted mono-(methacryloxy isopropyl)-ester of o-phthalic acid, methacryloxyisopropyl o-sulfobenzoate, methacryloxyisopropyl acid sulfosuccinate, methacryloxyethyl o-sulfobenzoate, or methacryloxyisopropyl sulfopropionate.

* * * * *